United States Patent
Bedford et al.

(10) Patent No.: US 11,259,966 B2
(45) Date of Patent: Mar. 1, 2022

(54) OPEN WOUND DRESSING WITH PROTECTION AGAINST CONTACT

(71) Applicants: Alexandria Bedford, Cazenovia, NY (US); James Doxtator, Syracuse, NY (US)

(72) Inventors: Alexandria Bedford, Cazenovia, NY (US); James Doxtator, Syracuse, NY (US)

( * ) Notice: Subject to any disclaimer, the term of this patent is extended or adjusted under 35 U.S.C. 154(b) by 502 days.

(21) Appl. No.: 15/658,645

(22) Filed: Jul. 25, 2017

(65) Prior Publication Data

US 2018/0021177 A1    Jan. 25, 2018

Related U.S. Application Data

(60) Provisional application No. 62/366,163, filed on Jul. 25, 2016.

(51) Int. Cl.
*A61F 13/00* (2006.01)
*A61F 13/02* (2006.01)

(52) U.S. Cl.
CPC .. *A61F 13/00017* (2013.01); *A61F 13/00063* (2013.01); *A61F 13/023* (2013.01); *A61F 13/0269* (2013.01); *A61F 2013/00157* (2013.01); *A61F 2013/00165* (2013.01); *A61F 2013/00272* (2013.01)

(58) Field of Classification Search
CPC ............. A61F 15/008; A61F 13/00017; A61F 2013/0074; A61F 2013/00157; A61F 2013/00165; A61F 13/00004; A61F 13/00008; A61F 13/00021; A61F 13/00063; A61F 13/023; A61F 13/0269; A61F 13/0063; A61F 2013/00272
USPC ......... 602/42, 46, 48, 52; 128/887, 888, 889
See application file for complete search history.

(56) References Cited

U.S. PATENT DOCUMENTS

| | | | | |
|---|---|---|---|---|
| 4,972,829 A | * | 11/1990 | Knerr | A61F 15/008 602/47 |
| 5,062,433 A | * | 11/1991 | Kummer | A41D 13/0506 128/888 |
| 5,758,662 A | * | 6/1998 | Hall | A61F 15/008 128/888 |
| 2005/0107732 A1 | * | 5/2005 | Boyde | A61F 15/008 602/41 |
| 2009/0069737 A1 | * | 3/2009 | Stapley | A61F 13/069 602/46 |
| 2010/0016462 A1 | * | 1/2010 | Clement | A61P 17/02 523/105 |
| 2011/0034888 A1 | * | 2/2011 | Aali | A61F 15/008 604/319 |
| 2011/0213287 A1 | * | 9/2011 | Lattimore | A61F 13/00021 602/46 |
| 2011/0237994 A1 | * | 9/2011 | Russ | A61F 13/00063 602/46 |
| 2015/0290043 A1 | * | 10/2015 | Antalek | A61F 13/02 602/46 |

* cited by examiner

*Primary Examiner* — Caitlin A Carreiro
(74) *Attorney, Agent, or Firm* — Bernhard P. Molldrem, Jr.

(57) ABSTRACT

A wound dressing for a burn or open wound is formed of a foam material body with an open center area. The thickness of the foam body creates a zone for air circulation and prevents contact with the wound. This may have a mesh, gauze or other air permeable cover over the open center area.

9 Claims, 3 Drawing Sheets

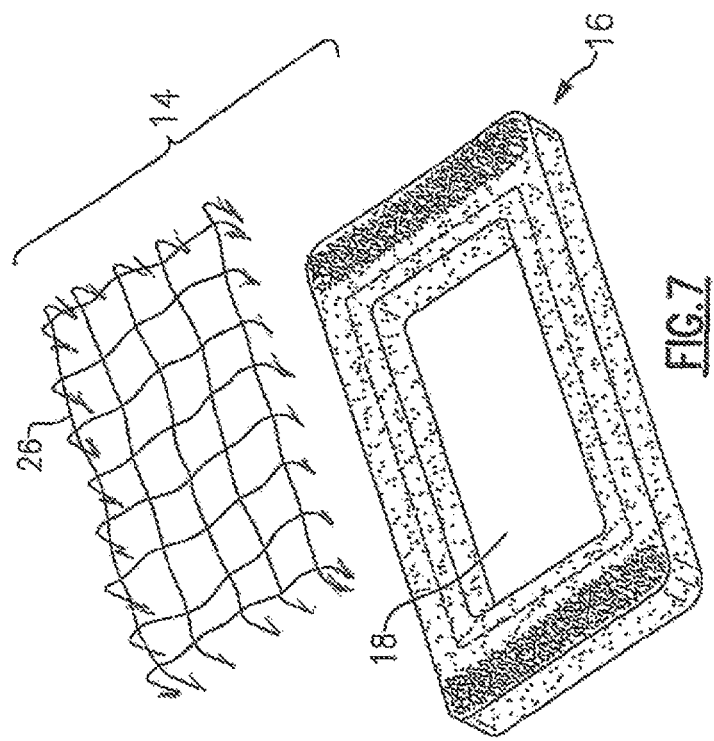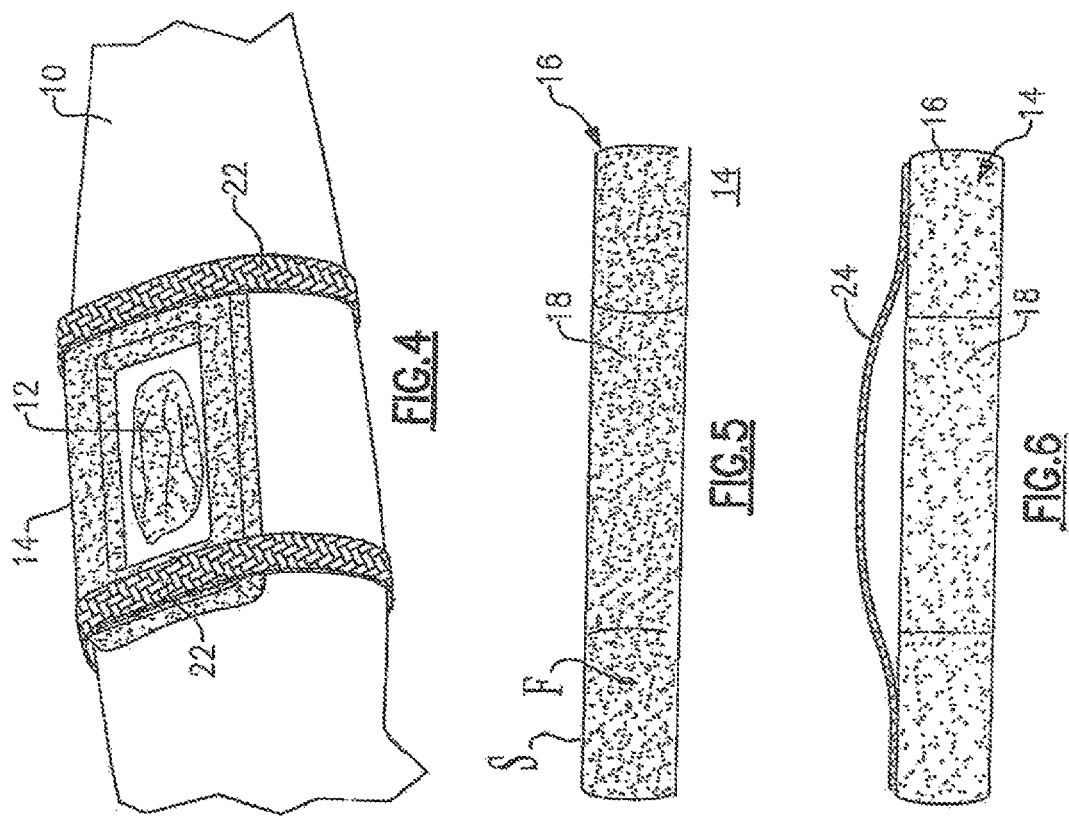

1

OPEN WOUND DRESSING WITH PROTECTION AGAINST CONTACT

Benefit is claimed under 35 U.S.C. 119(e) of our provisional application Ser. No. 62/366,163, filed Jul. 25, 2016, and which is incorporated by reference herein.

This invention is directed to wound dressing intended for patients with severe burns or open wounds where rubbing or other contact with the wound may result in re-opening the wound, and where wrapping the wound may prevent circulation of air and delay closure of the wound or impair healing.

Patients with burn injuries or severe wounds require sleep and bed rest, and it is important for these wounds to close and heal over quickly so that the skin can regenerate and heal. However, current wound dressing options may make it difficult for the patient to sleep or move because of the risk of rubbing against the wound, causing pain and also re-opening the wound. Bandages or gauze pads applied onto the wound also restrict circulation of air to the wound, so the wound closes and heals much more slowly. Current options for dressing the burn or similar wound involve wrapping with gauze or pre-packaged wet bandages, which do not address the issues of air circulation and healing mentioned just above.

The present invention involves a technique and wound dressing that creates a stand-off around the burn wound to avoid contact with the wound to allow the wound to close, and also to allow air to circulate to the wound which assists in the healing process.

Patients with severe wounds and burns have difficulty in sleeping and in moving about when the wound dressing is wrapped onto the wound, as any contact with the wound may re-open the wound, and because the dressing itself blocks air circulation. Also the wound can scab onto the gauze itself, resulting in re-injury or re-opening the wound upon removal of the dressing. The present invention addresses this by employing padding to the area outside the wound or burn. This allows the patient to move about and to sleep without limiting air circulation to the wound for healing. Accordingly, the wound can scab over and close, allowing the skin beneath to regenerate and heal. The dressing of this invention also provides better protection of the injured area during movement or during sleep.

BRIEF DESCRIPTION OF THE DRAWING

FIG. 4 shows the wound dressing of this embodiment with straps holding the wound dressing onto the patient's arm.

FIG. 5 is a cross-section of the wound dressing of this embodiment.

FIG. 6 is a side elevation showing an additional protective cover applied thereto.

FIG. 7 is a perspective showing a metal screen cover that can be applied over the open area of the wound dressing of this invention.

DETAILED DESCRIPTION

An embodiment of the invention can be understood from a discussion of FIGS. 1 to 4.

Figure 1:
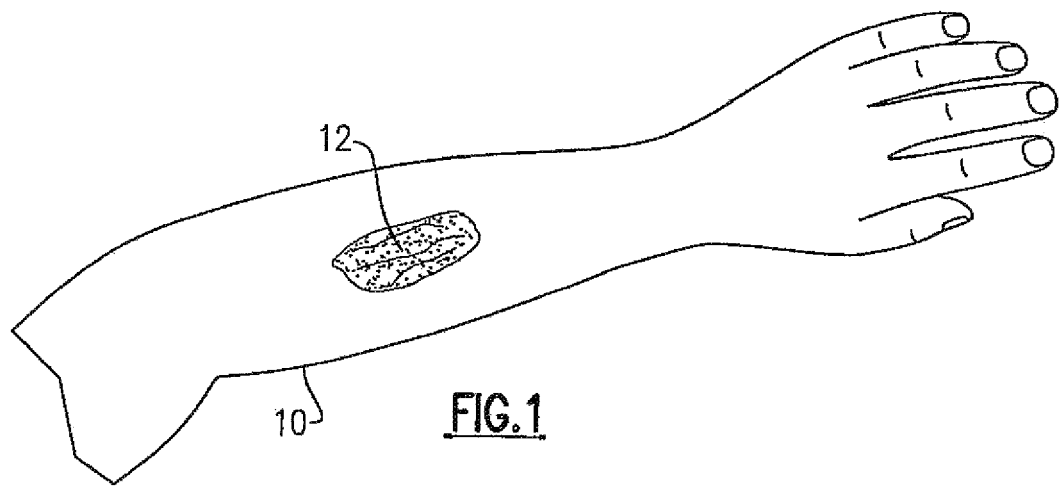
FIG. 1 illustrates a burn injury to a patient's arm.
Figure 2:
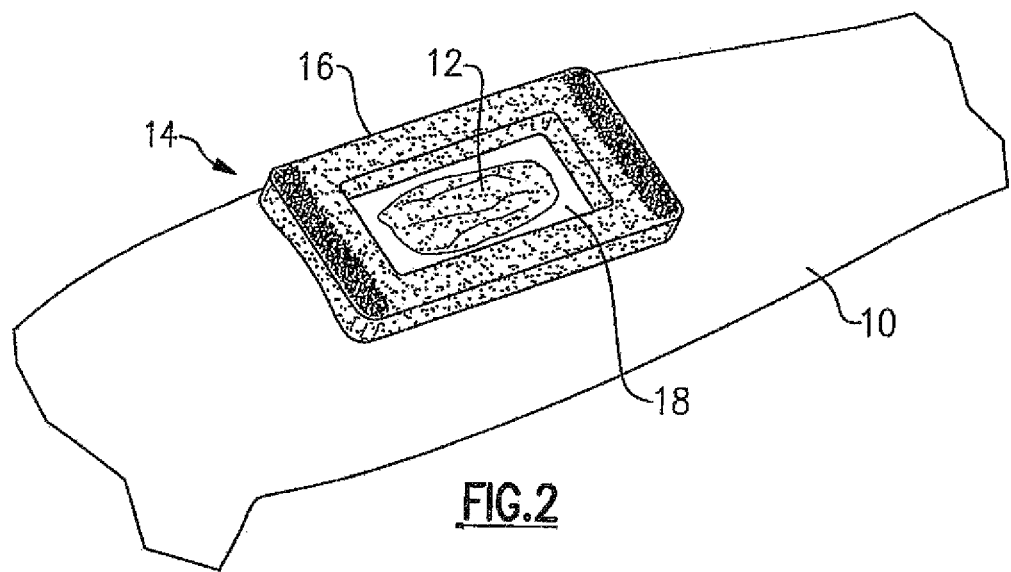
FIG. 2 shows the wound dressing of this invention applied onto the patient's skin around the area of the burn injury.
Figure 3:
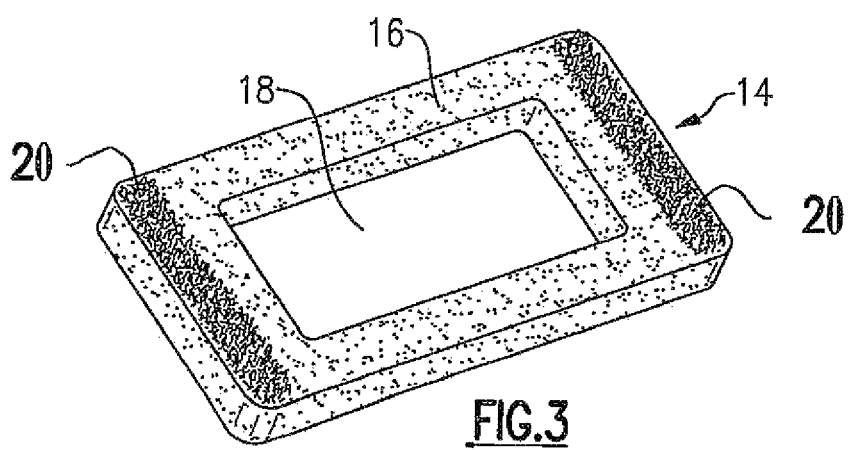
FIG. 3 shows the wound dressing according to one embodiment of the invention.

An injury may occur to a person, and to illustrate a typical injury, i.e., a scrape or burn 12 here appears on one arm 10 of a person. The dressing unit 14 of an embodiment of the invention has a main body portion 16, here a rectangular slab of a flexible closed-cell foam material with an open center or cutout area 18 framed by the main body portion 16. Favorably, the body portion is formed of a somewhat stiff but flexible foam plastic, approximately one-half inch to one inch in thickness. The cutout area 18 should be about one centimeter on each side larger than the wound site, i.e., the scrape or burn 12. The side of the body portion 16 that faces the person's skin can have a suitable adhesive applied to it, or may have medical double-sided tape, to attach the unit to the wearer's skin. Alternatively, the unit can be held in place with an elastic tape. As shown in FIGS. 2 and 3, the hook portion of a hook-loop fastener material 20 is applied onto opposite sides of the main body portion. Then, as shown in FIG. 4, straps 22 which may have loop-type material, are applied over the hook material, and the straps 22 hold the unit onto the wearer's arm. The open space of the cutout area 18 allows air to circulate to the scrape or burn, which is free to scab up as there is no bandage or gauze. The foam material should have approximately the stiffness of a kneeling pad of the type often used in gardening.

As illustrated in FIG. 5, the main body portion 16 is formed as a durable closed-cell foam material F of medical grade, and a water tight membrane or skin S is formed over some or all of its surfaces. This can contain an antibacterial agent. The foam pad of the body portion 16 with the membrane S may contain post-surgical protective materials, such as Betadine® (povidone iodide), topical pain reliever, a 30-day surface protectant, which may contain anti-microbial agents and/or antibiotics to assist in healing and to prevent-re-injury.

Medical adhesive or elastic tape can be used to secure the pad, rather than the hook-and-loop (Velcro) straps 22 as shown. Alternatively, a sticky gauze can be used for this. As shown in cross section in FIG. 6, a metal or tough plastic cover 24 can be affixed over the open center or cutout area 18 to protect the wound area. This may be required for wounds that are greater than about four inches across. The cover 24 may be a single piece, or may be formed of a number of strips of aluminum or another rigid material to protect the wound but not obstruct air flow. For some larger wounds, it may be necessary to attach the aluminum bars to a patch of a fabric, where each bar may have a barb to hold it in place on the fabric.

Alternatively, a panel 26 of a mesh or screen material (FIG. 7) may be used as a cover, with wires that can be pushed into the foam material to hold the mesh panel in place over the wound.

The padding by itself protects the burn or wound from contact and re-injury while still allowing air circulation during work or play activity, sleeping, or general movement. The foam padding surrounds the wound and serves as a stand-off to block contact with objects, so that nothing touches the wound as it is healing. The cover or screening can be secured over the open area 18 to protect the wound from debris, dust, or other intrusions. The rigid screen, cover or aluminum bars create a cage over the wound or burn 12, allowing freedom of movement, and providing for comfortable sleep for the patient, without risk of re-injury.

The padding should be between ½ inch and one inch, for most purposes, and typically about ¾ inch thick. The center opening 18 should allow for a 1 cm space around each edge of the burn or wound 12. The foam material may be cut way to enlarge or re-shape the center opening, i.e. cutout area 18 as needed, or to trim away the outside perimeter portion so that the unit fits comfortably to the body part where the wound or burn 12 is located. The hook-loop fastener material may be adhesive-backed Velcro strips, which can be applied to the body portion 16 of the unit after excess portions of the foam material have been trimmed away. Then Velcro straps can be used to hold the body portion 16 in place over the wound. For most applications, a thin layer of gauze (not shown) maybe secured to the top surface of the body portion 16 over the open cutout area 18, using a medical tape. The metal bars or screening as discussed above can be used in appropriate cases.

Other material, such as a styrene foam (Styrofoam) material, can be used as a spacing material, as could an inflatable ring, to protect the wound, injury or sore for better air circulation and faster healing. In some cases, a medical sleeve or stocking can be worn over the wound dressing, and may hold it in place in lieu of a strap or adhesive.

The wound dressing may be used for various post-surgical healing situations, e.g., stitches to close a laceration, eye surgery, dental and/or maxillofacial injuries, burns to any degree, cuts, puncture wounds for humans, pets, or livestock. For veterinary use, the dressing may be used to cover any type of open sore, wound or hot spot, and in addition a bitter anti-lick spray or liquid may be used on its exterior. The dressing may also be used for bed sores, insect or spider bites, or any other wound where air circulation is needed or helpful to the healing process. The unit may be used in conjunction with a cast where a broken bone is accompanied by wounds or skin abrasion. This dressing may also be helpful in cases of skin grafting, head injuries, chest-port sites, joint injuries, podiatric care such as foot injuries where rubbing the wound has to be prevented. The dressing may be applied before the cast is in place.

Many other medical and veterinary applications exist where the unit of this invention would be helpful in the healing of the injured person or animal. For animal injuries, an anti-lick solution can be applied to the foam pad.

Figure 8:
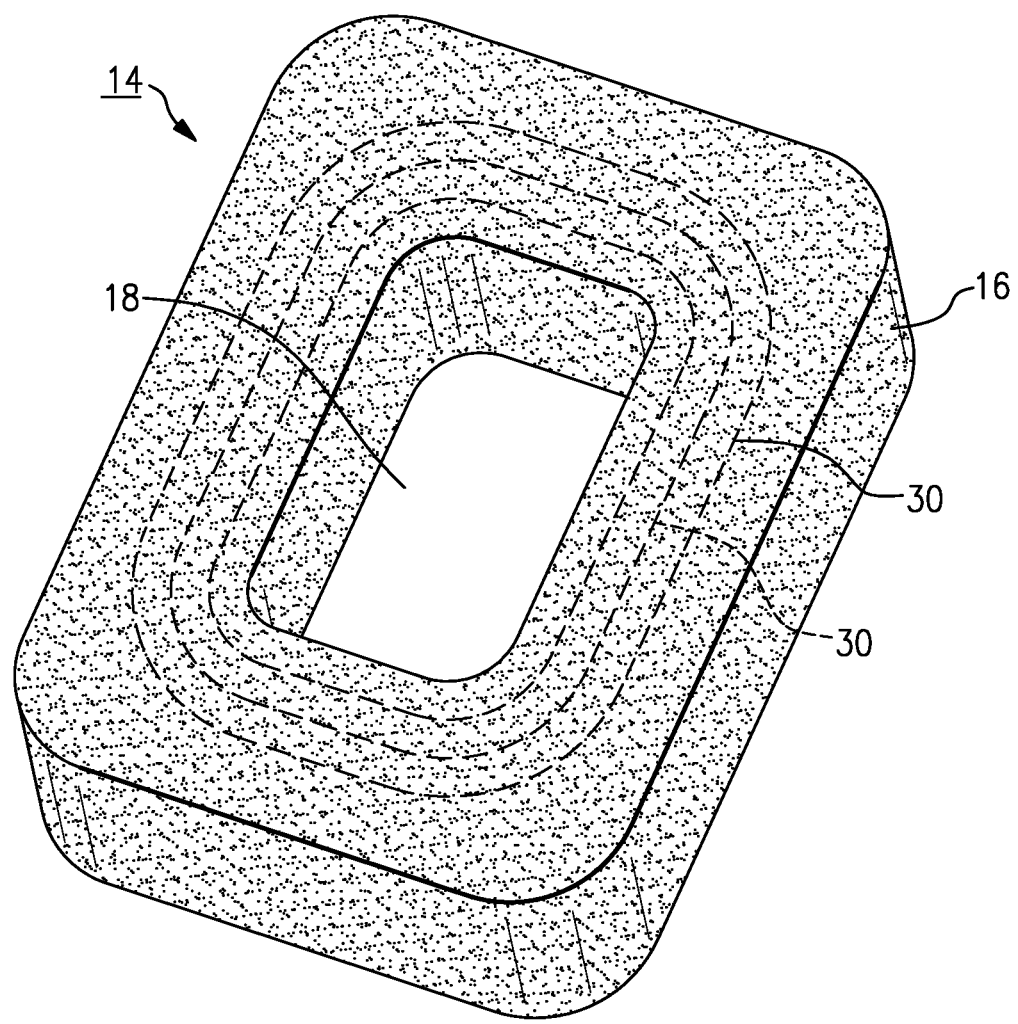
FIG. 8 illustrates an alternative embodiment.

FIG. 8 shows another dressing unit 14 with a main body portion 16 of a flexible closed cell foam material surrounding a central open area or cutout area 18. Favorably, the foam material is impregnated with an anti-infectant such as Betadine® (povidone iodide), or an antibiotic cream, and may also incorporate a skin moisturizer. Here area also shown plural rings of perforations 30 formed in the foam material and surrounding the open area 18, to permit portions of the material to be easily removed, for custom sizing, e.g., to enlarge the central open cutout area. The three rings of perforations 30 define three removable rings of the foam material, so that the dressing unit 14 can be modified to fit any of four different size wounds. After being placed over the wound, the dressing unit 14 may be covered with flexible mesh or a gauze wrap, as with the other embodiments. This dressing unit may be used on human patients or on veterinary patients.

What is claimed is:

1. A wound dressing adapted for protecting a burn or other injury to skin of a user, said wound dressing comprising:
a slab of a foam cushion material having a central cutout where the foam cushion material is absent, and with a lower surface configured to be in contact with the skin and with an upper surface adapted to be positioned away from the skin, and with said foam cushion material being approximately a half inch to one inch in thickness to serve as a standoff above the burn or other injury,
wherein said slab of foam cushion material is formed with a main body portion and has a plurality of series of perforations therein, each of said series of perforations being arranged as an annular series of perforations within said slab, and said plurality of series of perforations being configured to define a plurality of annular portions within said main body portion, each surrounding said central cutout, and wherein said plurality of series of perforations are configured to permit one or more of said annular portions of said foam cushion material to be removed to enlarge said central opening for custom sizing of the wound dressing to accommodate the burn or other injury within the central cutout;
means for securing the wound dressing to the skin with the wound dressing positioned so that the burn or other injury is centered within the central cutout; and
a protective cover, configured as a cage that is open to air flow therethrough and has a length and width configured to span across said central cutout, wherein said cage is formed from a plurality of rigid aluminum bars having barbed ends that are configured to be pushed into and penetrate the upper surface of said foam cushion material in areas of said foam cushion material surrounding said central cutout, and wherein said barbed ends are configured to hold and retain the rigid aluminum bars in the slab of foam cushion material to secure said cage in place over the burn or other injury to the skin.

2. The wound dressing of claim 1, wherein said foam cushion material is impregnated with a post-surgical protective material.

3. The wound dressing of claim 2, wherein said post-surgical protective material includes a bitter anti-lick spray or liquid.

4. The wound dressing of claim 1, wherein said slab of foam cushion material is impregnated with one or more of povidone iodide, topical pain reliever, and an anti-microbial or antibiotic agent to assist in healing and prevent re-injury.

5. The wound dressing of claim 1, wherein said means for securing the wound dressing to the skin includes hook/loop material portions affixed to the upper surface of said slab at opposite edges thereof across said central cutout from one another, and at least one strap which includes hook/loop material to attach to the hook/loop material portions on said slab.

6. A wound dressing adapted for protecting a burn or other injury to skin of a user, said wound dressing comprising:
a panel of a foam cushion material having a central cutout where the foam cushion material is absent and having a lower surface configured to be in contact with the skin and an upper surface adapted to be positioned away from the skin, and wherein said foam cushion material has a thickness of approximately a half inch to one inch to serve as a standoff from the burn or other injury;
means for securing the wound dressing to the skin with the wound dressing positioned so that the burn or other injury is centered within the central cutout; and
a protective cover, configured as a cage that is open to air flow therethrough and has a length and width configured to span across said central cutout, wherein said cage is formed from a plurality of rigid aluminum bars having barbed ends that are configured to be pushed into and penetrate the upper surface of said foam cushion material in areas of said foam cushion material surrounding said central cutout, and wherein said barbed ends are configured to hold and retain the rigid aluminum bars in the panel of foam cushion material to secure said cage in place over the burn or other injury to the skin.

7. The wound dressing of claim 6, wherein said panel of foam cushion material is formed of a medical grade closed-cell foam with a water-tight membrane formed over the upper and lower surfaces thereof.

8. The wound dressing of claim 7, wherein said means for securing the wound dressing to the skin includes hook/loop material portions affixed to the upper surface of said panel at opposite edges thereof across said central cutout from one another, and at least one strap which includes hook/loop material to attach to the hook/loop material portions on said panel.

9. The wound dressing of claim 6, wherein the protective cover further comprises a layer of gauze.

\* \* \* \* \*